(12) United States Patent
Akbarali et al.

(10) Patent No.: US 7,084,299 B2
(45) Date of Patent: Aug. 1, 2006

(54) PROCESS FOR PRODUCING IBUPROFEN SODIUM DIHYDRATE

(75) Inventors: Padiyath Mohammed Akbarali, New Mangalore (IN); Kuniyil Kulangara Vijaya Raj, New Mangalore (IN); Ramesh Sabu Gani, New Mangalore (IN); Sujatha Krishna, New Mangalore (IN); Sumangala Venkatrraman, New Mangalore (IN); Manjathur Mahalinga, New Mangalore (IN)

(73) Assignee: Strides Research and Specialty Chemicals Limited, New Mangalore (IN)

( * ) Notice: Subject to any disclaimer, the term of this patent is extended or adjusted under 35 U.S.C. 154(b) by 0 days.

(21) Appl. No.: 11/078,319

(22) Filed: Mar. 14, 2005

(65) Prior Publication Data

US 2005/0272818 A1    Dec. 8, 2005

Related U.S. Application Data

(63) Continuation of application No. PCT/IN04/00160, filed on Jun. 7, 2004.

(51) Int. Cl.
    *C07C 53/134*    (2006.01)
(52) U.S. Cl. ..................................................... 562/496
(58) Field of Classification Search ................. 562/496
    See application file for complete search history.

(56) References Cited

U.S. PATENT DOCUMENTS 6,525,214 B1    2/2003    Armitage et al.

*Primary Examiner*—J. Parsa
(74) *Attorney, Agent, or Firm*—Neifeld IP Law, PC

(57) ABSTRACT

Disclosed herein is a novel process for producing Sodium dihydrate salt of Ibuprofen of Formula (Structure I) by treating a salt of long chain carboxylic acid of Formula (Structure III) with Ibuprofen of Formula (Structure II) in the presence of an aqueous organic solvent.

6 Claims, No Drawings

PROCESS FOR PRODUCING IBUPROFEN SODIUM DIHYDRATE

CROSS REFERENCE TO RELATED APPLICATIONS

This U.S. application Ser. No. 11/078,319 filed on Mar. 14, 2005 is a continuation of International Application No. PCT/IN04/00160, filed Jun. 7, 2004.

FIELD OF THE INVENTION

In general, this invention relates to a process for producing an alkali metal salt of Ibuprofen. More particularly, this invention relates to a novel process for producing sodium dihydrate salt of Ibuprofen.

BACKGROUND OF THE INVENTION

The major problem of developing pharmaceutical formulations of Ibuprofen is to address its poor solubility in water. Sodium dihydrate salt of Ibuprofen, the compound of Formula (Structure I), is an alkali metal salt of Ibuprofen which is freely soluble in water. Therefore, it is a good candidate for preparing a pharmaceutical formulation having better bioavailability. It is a very effective Non steroidal anti-inflammatory drug (NSAID), analgesic (pain reliever), and antipyretic (fever reducer). NSAID is the general term used for a group of drugs that are effective in reducing inflammation and pain.

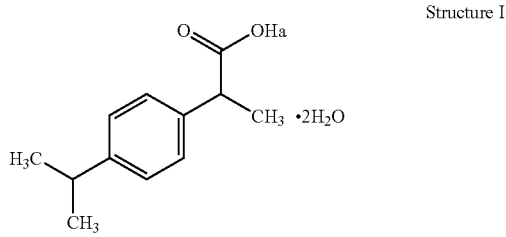

Structure I

Several processes are known for the preparation of Sodium dihydrate salt of Ibuprofen. The known processes include the method of producing Sodium dihydrate salt of Ibuprofen by using different base for treating with Ibuprofen, different organic solvents as reaction medium, different experimental parameters etc.

Japanese Patent No. 53044538 to Kiyaoura, et al., (Mitsui Toatsu Chemicals Inc., Japan) describes the preparation of sodium α-(4-isobutylphenyl) propionate by treating ibuprofen with a mixture of sodium hydroxide and 5% Pd/C in n-tetradecane by autoclaving at 200° C. for 1.5 hr. This method provides only sodium ibuprofen, which is not in hydrate form and is expensive due to the usage of Pd/C catalyst.

U.S. Pat. No. 4,859,704 to Haas, (Oratech Pharmaceutical Development Corporation, Princeton, N.J.) describes the method of making alkali metal salt of ibuprofen by treating ibuprofen with alkali metal carbonate in water media at an elevated temperature of 55–60° C. This method involves the evolution of $CO_2$ gas, which may lead to pressurization inside the reactor. Although method is simple the pressurization due to the evolution of $CO_2$ gas makes the process less attractive.

U.S. Pat. No. 5,969,181 to Breitenbach, et al., describes the method of preparing the sodium salt of ibuprofen racemate by reacting ibuprofen with sodium carbonate in the melt in an extruder. This method gives ibuprofen sodium without water of crystallization and also requires intermeshing twin screw extruder.

U.S. Pat. No. 6,525,214 to Armitage, et al., describes the preparation of pure enantiomeric salt of ibuprofen such as S(+)sodium 2-(4-isbutylphenyl) propionic acid dihydrate and S(−)sodium 2-(4-isbutylphenyl) propionic acid dihydrate by treating S(+)2-(4-isbutylphenyl) propionic acid [S(+)ibuprofen] and S(−)2-(4-isbutylphenyl) propionic acid [S(−)ibuprofen] with sodium hydroxide in aqueous media and the precipitation of the product in acetone.

The invention disclosed herein demonstrates simple, economical and a commercially viable process for producing Sodium dihydrate salt of Ibuprofen using suitable salt and solvents.

SUMMARY OF THE INVENTION

In one preferred embodiment of the present invention, there is provided a novel process for producing Sodium dihydrate salt of Ibuprofen by treating Ibuprofen with salt of long chain carboxylic acid to make the process simple and economical.

In another preferred embodiment of the present invention, there is provided a novel process for producing Sodium dihydrate salt of Ibuprofen, wherein the process comprises of, dissolving predetermined amount of Ibuprofen in an organic solvent and treating the same with an aqueous solution of salt of long chain carboxylic acid, evaporating the solvent and precipitating the resulting product in desirable quantity of acetone.

In one another preferred embodiment of the present invention, there is provided a novel process for producing Sodium dihydrate salt of Ibuprofen, wherein the organic solvent used for dissolving the Ibuprofen is selected from the group comprising tetrahydrofuran, ethanol, acetone.

In yet another preferred embodiment of the present invention, there is provided a novel process for producing Sodium dihydrate salt of Ibuprofen, wherein the organic solvent for dissolving the Ibuprofen can be recovered from the reaction mixture and reused.

In still another preferred embodiment of the invention, there is provided a novel process for producing Sodium dihydrate salt of Ibuprofen, wherein the process comprises of treating Ibuprofen with salt of long chain carboxylic acid via exchanging the metal part of salt of long chain carboxylic acid with ibuprofen in aqueous medium at room temperature.

In yet another preferred embodiment of the invention, there is provided a novel process for producing Sodium dihydrate salt of Ibuprofen, wherein the process comprises of dissolving 1 mole of Ibuprofen in 2 volume of tetrahydrofuran, stirring the same with 1 mole of salt of long chain carboxylic acid in 1 volume of aqueous medium for 1 hr at 28° C. and then for 6 hrs at room temperature, evaporating the solvent and precipitating the resulting product in 10 volume of acetone.

In one another preferred embodiment of the invention, there is provided a novel process for producing Sodium dihydrate salt of Ibuprofen, wherein the process comprises of dissolving 1 mole of Ibuprofen in 2 volume of ethanol, stirring the same with 1 mole of salt of long chain carboxylic acid in 1 volume of aqueous medium for 1 hr at 28° C. and then for 6 hrs at room temperature, evaporating the solvent and precipitating the resulting product in 10 volume of acetone.

In yet another preferred embodiment of the invention, there is provided a novel process for producing Sodium dihydrate salt of Ibuprofen, wherein the process comprises of dissolving 1 mole of Ibuprofen in 5 volume of acetone, stirring the same with 1 mole of salt of long chain carboxylic acid in 5 volume of aqueous acetone for 1 hr at 28° C. and then for 6 hrs at room temperature, chilling the solution and precipitating the resulting product in 10 volume of acetone.

DETAILED DESCRIPTION OF THE INVENTION

The disclosed embodiment of the present invention deals with a novel process for the preparation of Sodium dihydrate salt of Ibuprofen of Formula 1 that has advantages over prior art processes in that it obviates the formation of gaseous byproduct, which is undesirable during the commercial manufacturing and make it simple, economical and commercially viable process.

A process for producing Sodium dihydrate salt of Ibuprofen of Formula (Structure I) has been provided. The process comprising of treating a salt of long chain carboxylic acid of Formula (Structure III) with Ibuprofen of Formula (Structure II) in presence of suitable organic solvent. Aforesaid reaction is carried out by dissolving 1 mole of ibuprofen of Formula (Structure II) in 2 volume of organic solvents such as tetrahydrofuran, ethanol and then stirring with 1 mole of salt of long chain carboxylic acid of Formula (Structure III) in 1 volume of double distilled water/and corresponding solvent for 1 hr at 28° C. and for 6 hrs at room temperature. The solvent is then evaporated and thick syrup is then poured to 10 volume acetone and product is recovered by filtration.

Also 5 volume acetone is used for dissolving the Ibuprofen of Formula (Structure II) and treating with long chain carboxylic acid of Formula (Structure III) in aqueous acetone, and then chilling the resultant solution and precipitating the product in acetone.

Preferred embodiments of the present invention have been illustrated in the following reaction scheme:

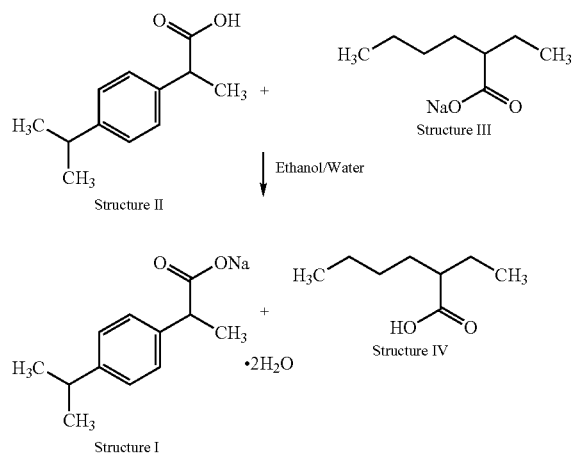

The byproduct which is long chain carboxylic acid of Formula (Structure IV) can be removed by acetone. Drying of the product at 40–50° C. for 1 hr gives a white crystalline material, which is freely soluble in water and has got a loss on drying of 12–15% that indicates the formation of ibuprofen sodium dihydrate. IR and UV spectra confirm with the standard product available in the market.

The HPLC assay of the product showed 99% with 0.2% 2-(4-isobutyryl phenyl) propionic acid and a total other impurities of 0.8%. Specific rotation ($C=0.1_{water}$) was found to be between +0.05 and −0.05 for the product.

The Salt of long chain carboxylic acid of Formula (Structure III) used in the present invention is sodium salt of 2-ethyl hexanoic acid which has very good solubility in organic solvent. Its solubility is high in tetrahydrofuran.

The resulting Sodium dihydrate salt of Ibuprofen of Formula (Structure I), which is prepared by a novel process disclosed in the present invention is very effective for reducing inflammation and pain. NSAIDs also inhibit the body's production of prostaglandins and other compounds such as cyclooxygenase, lipoxygenase, leukotrienes, and lysosomal enzymes that sensitize pain receptors and stimulate inflammatory responses.

The resulting Sodium dihydrate salt of Ibuprofen of Formula (Structure I), which is prepared by a novel process disclosed in the present invention, can be used for the preparation of different pharmaceutical formulations and dosage forms, such as tablets, capsules, liquids or parenterals.

Preferred embodiments are further illustrated in the following examples:

EXAMPLE 1

206.28 g (1 mole) ibuprofen is dissolved in 412 ml of THF. To this 166 g (1 mole) of sodium-2-ethyl hexanoate in 166 ml of double distilled water is added dropwise for 1 hr at 28° C. and then stirred for 6 hrs. The clear solution is filtered and THF is then distilled out completely to get a syrupy liquid. Syrupy liquid is then slowly poured in to 2062 ml of acetone and stirred for 1 hr. The product is then filtered and washed with 100 ml acetone and suck dried. Then the product was dried at 45–50° C. under vacuum for 1 hr to get 185 g of the product with moisture content of 13.01% and an LOD of 14.24%. HPLC assay of the product showed 99% and a specific rotation +0.04 in water.

EXAMPLE 2

206.28 g (1 mole) ibuprofen is dissolved in 412 ml of ethanol. To this 166 g (1 mole) of sodium-2-ethyl hexanoate in 166 ml of double distilled water is added dropwise for 1 hr at 28° C. and then stirred for 6 hrs. The clear solution is filtered and ethanol is then distilled out completely to get a syrupy liquid. Syrupy liquid is then slowly poured in to 2062 ml of acetone and stirred for 1 hr. The product is then filtered and washed with 100 ml acetone and suck dried. Then the product was dried at 45–50° C. under vacuum to get 183 g of the product with moisture content of 13.03% and an LOD of 14.25%. HPLC assay of the product showed 99% and a specific rotation +0.039 in water.

EXAMPLE 3

206.28 g (1 mole) ibuprofen is dissolved in 1030 ml of acetone. To this 166 g (1 mole) of sodium-2-ethylhexanoate in 1030 ml acetone and 36 ml of double distilled water is added dropwise for 1 hr at room temperature and then stirred for 6 hrs. The clear solution is filtered and chilled to 0° C. The product is then filtered and washed with 100 ml acetone and suck dried. Then the product was dried at 45–50° C.

under vacuum to get 180 g of the product with moisture content of 13.1% and an LOD of 14.3%. HPLC assay of the product showed 99% and a specific rotation +0.04 in water.

Certain modifications and improvements of the disclosed invention will occur to those skilled in the art without departing from the scope of invention, which is limited only by the appended claims.

We claim:

1. A process for producing sodium dihydrate salt of ibuprofen, the process comprising:

dissolving 1 mole of ibuprofen in 2 volume of organic solvent, stirring with 1 mole of salt of a long chain carboxylic acid in 1 volume of double distilled water/ and corresponding solvent for 1 hr at 28° C. and for 6 hrs at room temperature, evaporating the solvent and precipitating the resultant product in 10 volume acetone, wherein the said salt of long chain carboxylic acid is sodium-2-ethyl hexanoate.

2. The process according to claim 1, wherein the organic solvent is selected from a group comprising, tetrahydrofuran, ethanol or acetone.

3. The process according to claim 1, wherein the organic solvent is tetrahydrofuran.

4. The process according to claim 1, wherein the organic solvent is ethanol.

5. A process for producing sodium dihydrate salt of ibuprofen, the process comprising:

dissolving 1 mole of ibuprofen in 5 volume of an organic solvent, stirring with 1 mole of salt of a long chain carboxylic acid in 1 volume of aqueous acetone for 1 hr at 28° C. and for 6 hrs at room temperature, chilling the solution and precipitating the resultant product.

6. The process according to claim 5 wherein the said salt of long chain carboxylic acid is sodium-2-ethyl hexanoate.

* * * * *